(12) United States Patent
Overeem et al.

(10) Patent No.: US 7,501,517 B2
(45) Date of Patent: Mar. 10, 2009

(54) PROCESS FOR MAKING MONTELUKAST AND INTERMEDIATES THEREFOR

(75) Inventors: Arjanne Overeem, Ede (NL); Reinerus G. Gieling, Nijmegen (NL); Jie Zhu, Nijmegen (NL); Lambertus Thijs, Wijchen (NL)

(73) Assignee: Synthon IP, Inc., Gainesville, VA (US)

( * ) Notice: Subject to any disclaimer, the term of this patent is extended or adjusted under 35 U.S.C. 154(b) by 405 days.

(21) Appl. No.: 11/081,695

(22) Filed: Mar. 17, 2005

(65) Prior Publication Data
US 2005/0245569 A1 Nov. 3, 2005

Related U.S. Application Data

(60) Provisional application No. 60/584,675, filed on Jul. 2, 2004, provisional application No. 60/566,603, filed on Apr. 30, 2004.

(51) Int. Cl.
C07D 215/38 (2006.01)
(52) U.S. Cl. ........................ 546/174; 514/311
(58) Field of Classification Search ................ 546/174; 514/311
See application file for complete search history.

(56) References Cited

U.S. PATENT DOCUMENTS

| | | | |
|---|---|---|---|
| 5,266,568 | A | 11/1993 | Belley et al. |
| 5,270,324 | A | 12/1993 | Zamboni et al. |
| 5,523,477 | A | 6/1996 | King et al. |
| 5,565,473 | A | 10/1996 | Belley et al. |
| 5,585,115 | A | 12/1996 | Sherwood et al. |
| 5,614,632 | A | 3/1997 | Bhupathy et al. |
| 5,856,322 | A | 1/1999 | Belley et al. |
| 5,869,673 | A | 2/1999 | Tung et al. |
| 6,063,802 | A | 5/2000 | Winterborn |
| 6,320,052 | B1 | 11/2001 | Bhupathy et al. |
| 2004/0265375 | A1 | 12/2004 | Platteeuw et al. |
| 2005/0107426 | A1 | 5/2005 | Overeem et al. |
| 2005/0245568 | A1 | 11/2005 | Overeem et al. |

FOREIGN PATENT DOCUMENTS

| | | | |
|---|---|---|---|
| CN | 1420113 | * | 5/2003 |
| CN | 1428335 | * | 7/2003 |
| EP | 0 480 717 | | 4/1992 |
| WO | WO 95/18107 | | 7/1995 |

OTHER PUBLICATIONS

"An Efficient Synthesis of LTD₄ Antagonsit L-699,392" by A.O. King et al., *J. Org. Chem.* 1993, 58, pp. 3731-3735.

* cited by examiner

*Primary Examiner*—D. Margaret Seaman
(74) *Attorney, Agent, or Firm*—Mark R. Buscher

(57) ABSTRACT

A process for making montelukast, a pharmaceutically useful compound of the following formula and salts thereof:

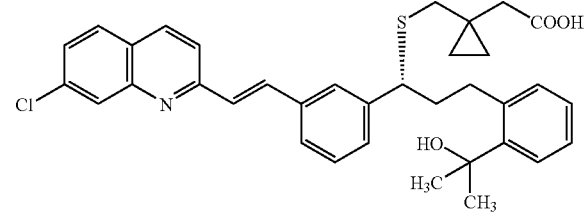

using a compound of formula (4)

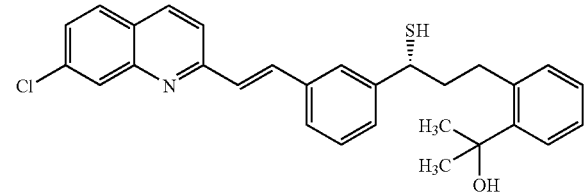

is provided.

14 Claims, No Drawings

PROCESS FOR MAKING MONTELUKAST AND INTERMEDIATES THEREFOR

This application claims the benefit of priority under 35 U.S.C. § 119(e) from U.S. provisional application 60/566,603, filed Apr. 30, 2004, and from U.S. provisional application 60/584,675, filed Jul. 2, 2004, the entire contents of each provisional application being incorporated herein by reference.

BACKGROUND OF THE INVENTION

The present invention relates to a process for the synthesis of montelukast, a pharmaceutical agent, as well as to intermediates useful in the process.

Montelukast, chemically [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropane acetic acid, has a structure represented by formula (1):

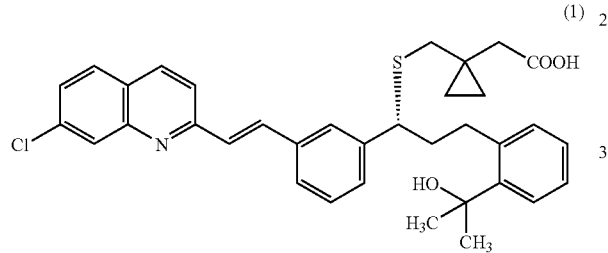

(1)

Montelukast monosodium salt (montelukast sodium) is commonly used for treatment of asthma. It is marketed under the brand name SINGULAIR® (Merck) in the form of oral tablets, chewable tablets, and granules.

U.S. Pat. No. 5,565,473 to BELLEY et al. (see also corresponding EP 0 480 717) discloses a genus of pharmaceutically useful compounds that encompasses montelukast and salts thereof. Example 161 in connection with example 146 of U.S. Pat. No. 5,565,473 discloses the synthesis of montelukast sodium as follows:

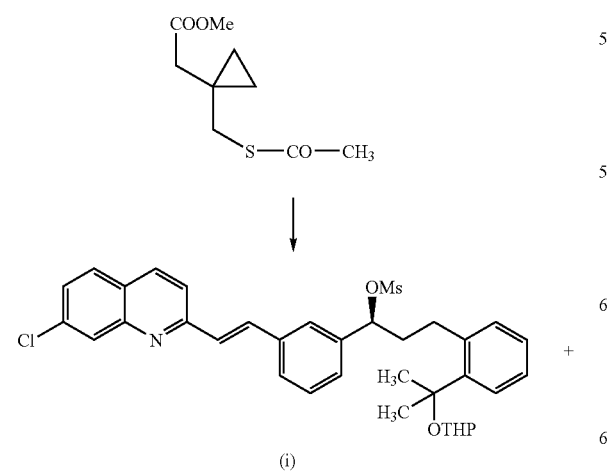

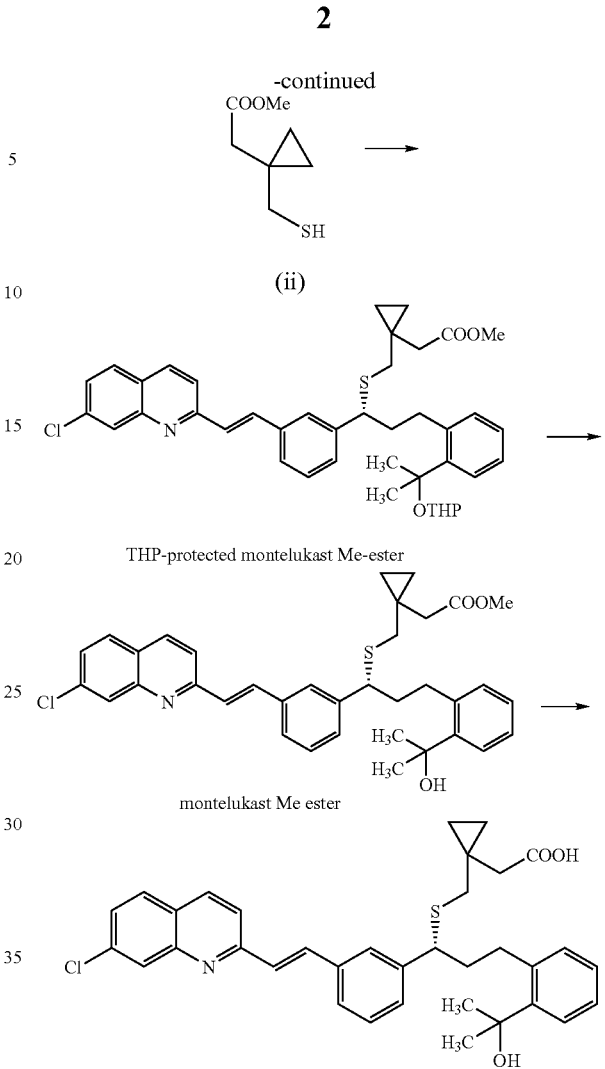

THP as used herein means tetrahydropyranyl group, typically of the formula:

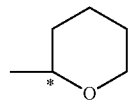

wherein the asterisk indicates a chiral carbon atom.

Many other synthetic schemes are proposed in U.S. Pat. No. 5,565,473 for making montelukast and/or other compounds. For instance, Method M of U.S. Pat. No. 5,565,473, if applied to montelukast, would appear to follow the scheme:

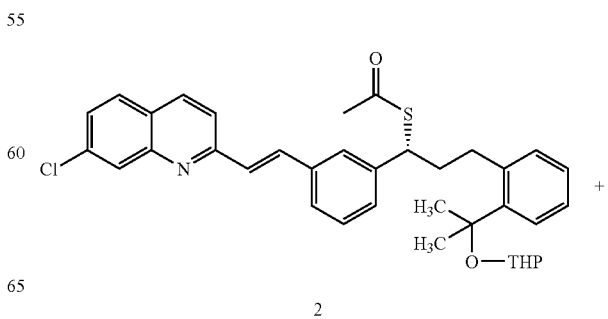

-continued

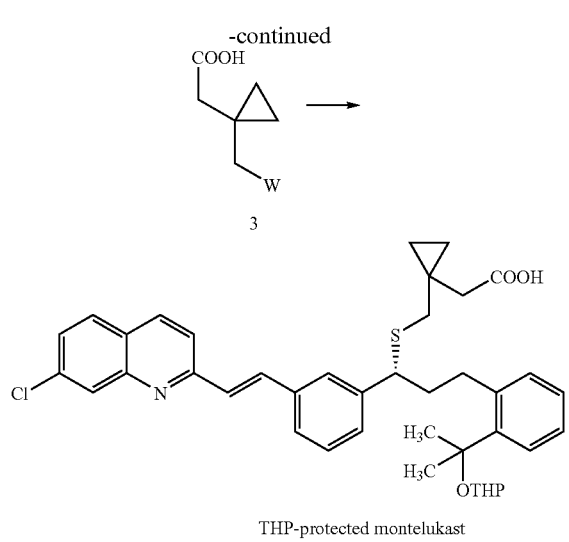

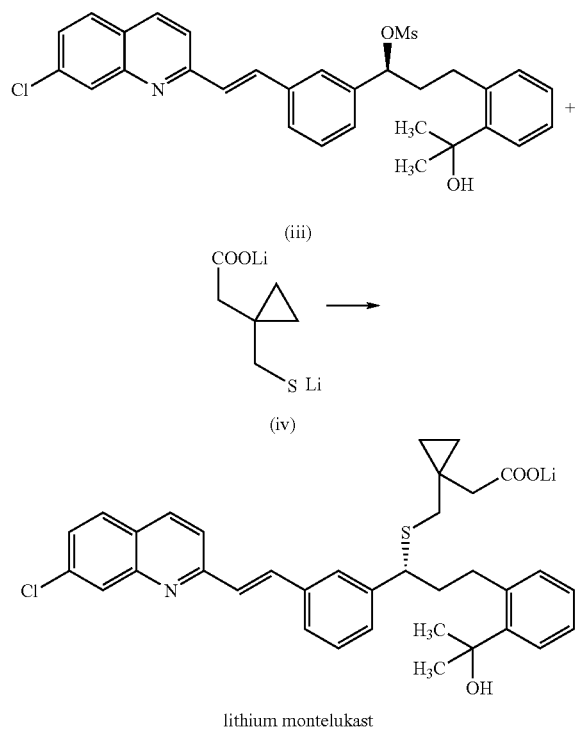

THP-protected montelukast

The S—CO bond in the compound of formula (2) would first be cleaved by hydrazine or sodium methanolate to form an —SH group and then a side chain donor, shown here for montelukast as a cyclopropane acetic acid derivative (3), would be reacted therewith to form THP-protected montelukast. W is a leaving group such as a chloro-, bromo- or mesylate group. The side chain donor reaction is carried out under the presence of a base such as cesium carbonate. The THP-protected montelukast would then be converted to montelukast in this hypothetical scheme.

Another approach has been applied in WO 95/18107. Here a crystalline alkyl- or aryl-sulfonate intermediate compound, preferably a methane sulfonate compound (iii), is reacted with a dilithium anion of 1-(mercaptomethyl)cyclopropane-1-acetic acid (iv) as represented below:

lithium montelukast

In general, the above described syntheses of montelukast comprise a reaction between a quinolinylethenylphenyl building block (e.g. compounds (i), (iii) or (2)) and a cyclopropane carboxylate building block (e.g. compounds (ii), (iv) or (3)). The above-processes, however, have various drawbacks and it would be desirable to provide a different, useful process for making montelukast and its salts, especially a process that could be performed on an industrial scale.

SUMMARY OF THE INVENTION

The first aspect of the invention relates to a process for making montelukast and its salts which comprises converting a compound of formula (4)

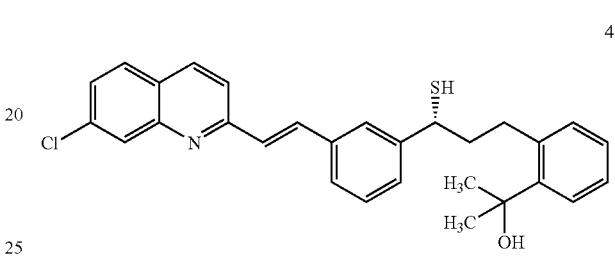

(4)

into montelukast of formula (1)

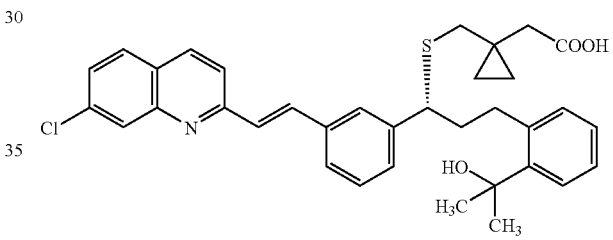

or a salt thereof.

Generally the conversion involves reacting the compound of formula (4)

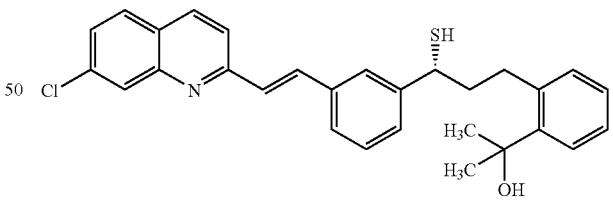

(4)

with a compound of formula (5)

(5)

wherein R is hydrogen or C1-C4 alkyl group, and L is a leaving group typically a halogen or an alkyl- or aryl-sulfonyloxy group such as chloro, bromo, mesyloxy, besyloxy or tosyloxy group. The reaction can take place in an inert solvent under the atmosphere of an inert gas. If the product of such reaction is an ester, e.g. R is an alkyl, then the compound can be further reacted; e.g. hydrolyzed, to convert the ester compound into montelukast acid or salt.

Another aspect of the invention relates to a process for making the cyclopropane derivative of formula (5) using a compound of formula (9).

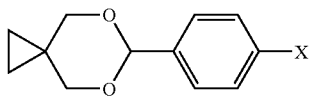

(9)

The process typically comprises:

a) reacting 1,1-cyclopropane dimethanol of formula (7)

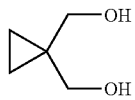

(7)

with a benzaldehyde compound of formula (8)

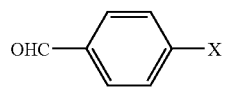

(8)

wherein X is hydrogen, hydroxy, methoxy, chloro, bromo, fluoro, methyl, trifluoromethyl or nitro group, to yield a cyclic acetal compound of formula (9);

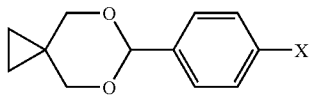

(9)

b) converting, in the presence of an oxidant, the compound of formula (9) to a mono-benzoyl nitrile compound of formula (11);

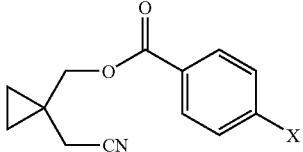

(11)

c) deprotecting the OH— group and hydrolyzing the cyano group in the compound of formula (11) to form a hydroxymethyl carboxylic acid compound of formula (13);

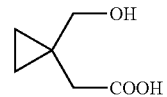

(13)

d) esterifying the acid compound of formula (13) with a C1-C4 alcohol in the presence of an acid to yield an ester compound of formula (14)

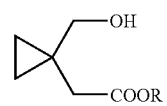

(14)

wherein R is a C1-C4 alkyl group; and e) converting the ester compound of formula (14) into a compound of formula (5)

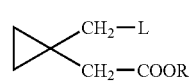

(5)

wherein R is a C1-C4 alkyl group and L is a leaving group.

A further aspect of the invention relates to using a compound of formula (21)

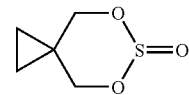

(21)

in making the cyclopropane derivative of formula (5). The process typically comprises:

a) reacting 1,1-cyclopropane dimethanol of formula (7)

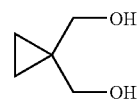

(7)

with thionyl chloride or with a dialkyl sulfite, wherein each alkyl group is a C1-C4 alkyl, to yield a compound of formula (21);

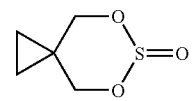

(21)

b) reacting said compound of formula (21) with an alkali metal cyanide to form a compound of formula (12);

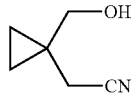

c) hydrolyzing the cyano group in the compound of formula (12) to form a hydroxymethyl carboxylic acid compound of formula (13);

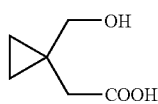

d) esterifying the acid compound of formula (13) with a C1-C4 alcohol in the presence of an acid to yield an ester compound of formula (14)

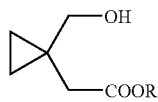

wherein R is a C1-C4 alkyl group; and e) converting said ester compound of formula (14) into a compound of formula (5)

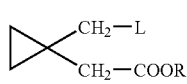

wherein R is a C1-C4 alkyl group and L is a leaving group.

Another aspect of the invention relates to compounds of formula (4) and (6), optionally in isolated and/or purified form, and to their use as intermediates in forming montelukast and its salts.

DESCRIPTION OF THE INVENTION

The present invention provides a new process for making montelukast and its salts, from a compound of formula (4). The conversion of the compound (4) into montelukast of formula (1) or a salt thereof generally comprises a condensation reaction with a compound of formula (5). As the compound (4) is a reactive compound, particularly under the presence of oxygen and under conditions necessary for nucleophilic substitution, and can easily decompose to form a disulphide, it is advantageous that the compound (4) is made in situ from a compound of formula (6) and reacts under conditions that suppress the undesired decomposition. The reaction scheme can be expressed as follows:

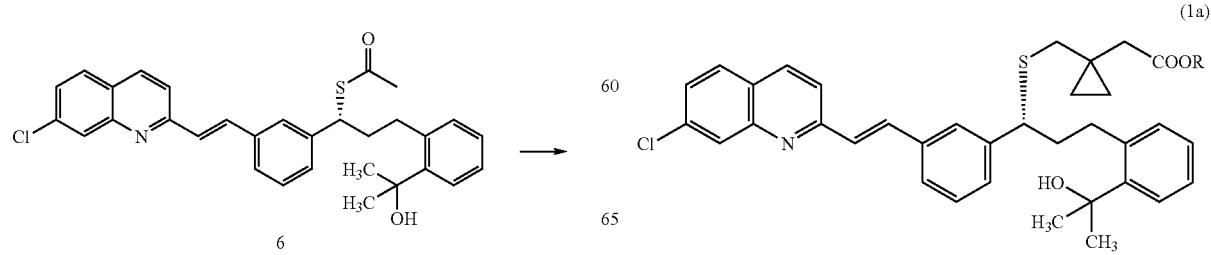

In an advantageous mode, the compound of formula (6) is converted into (4) by a cleaving reaction using a hydrazine or sodium methoxide in an inert aprotic solvent, e.g. in acetonitrile, under atmosphere of an inert gas, such as nitrogen or argon, at temperatures at or close to ambient, preferably at about 0° C. After the cleavage reaction and the formation of the —SH moiety and hence compound (4), the reaction mixture is treated with compound (5) and a base, either in solid state or in a solvent. If compound (5) and/or the base are in a solvent, preferably the solvent is the same as used in the preceded step of cleavage. Typically the solution or suspension containing the compound (5) and/or base should preferably also be saturated by an inert gas. A suitable base is an alkaline metal hydroxide or carbonate such as cesium carbonate. The reaction proceeds at temperatures at or close to ambient, e.g. at 0-20° C., and may be monitored by ordinary methods such as HPLC or TLC. After conventional treatment of the reaction mixture with the aim to remove inorganic by-products, the product may be isolated by conventional methods and optionally purified, e.g. by column chromatography, etc.

When the R in formula (5) comprises a C1-C4 alkyl group, which is a preferred embodiment, the product of the above process is a C1-C4 ester of montelukast of formula (1a), wherein R is C1-C4 alkyl group:

-continued

1a/1 R = —CH₃
1a/2 R = —CH₂—CH₃
1a/3 R = —CH₂—CH₂—CH₃
1a/4 R = —CH(CH₃)₂
1a/5 R = —CH2—CH₂—CH₂—CH₃
1a/6 R = —CH(CH₃)—CH₂—CH₃
1a/7 R = —CH₂—CH(CH₃)—CH₃
1a/8 R = —C(CH₃)₃

The preferred ester is montelukast ethyl ester, e.g. R is ethyl as shown in compound (1a/2). Within the process of the invention, the ester may be produced in its isolated form, i.e. in oily or solid state, essentially free from solvents and side products, which substantially improves its handling and storage properties and also allows the preparation of montelukast acid or its salt in high yield and good purity.

The ester of montelukast can be converted into montelukast or its salt by known techniques, e.g., by following the de-esterification or hydrolysis procedure as disclosed in Example 146 of the EP 480717. The final product of such procedure is a montelukast salt, e.g. montelukast sodium. However, montelukast salt may be converted into an acid form of montelukast, including the solid state forms of the montelukast acid as disclosed in U.S. patent application Ser. No. 10/960,639, filed Oct. 8, 2004, entitled "Solid State Montelukast," the entire contents of which are incorporated herein by reference.

The compound of formula (6) can be made by, inter alia, two reaction pathways. The first pathway is set forth in the following reaction scheme:

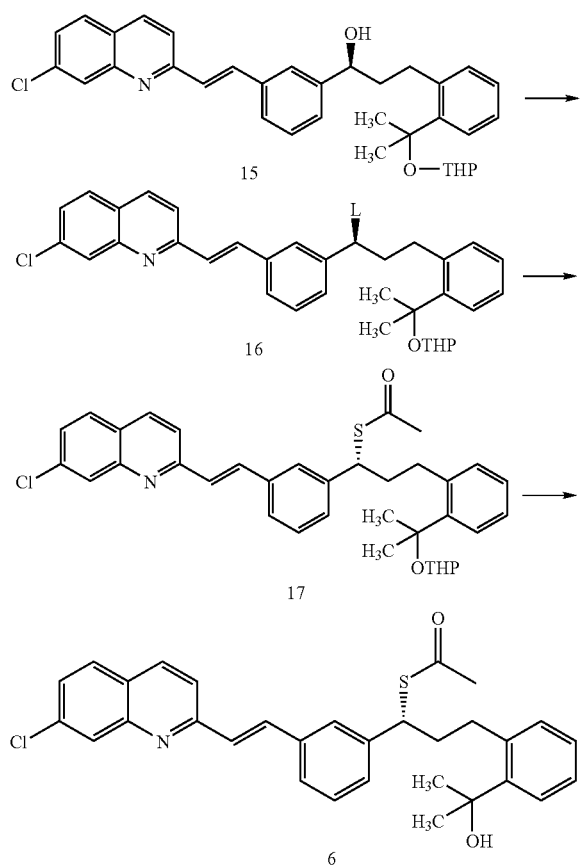

The first pathway starts from the THP-protected compound of formula (15). This compound is known in the prior art (see Example 146 of EP 480717) and may be prepared from a diol (15a).

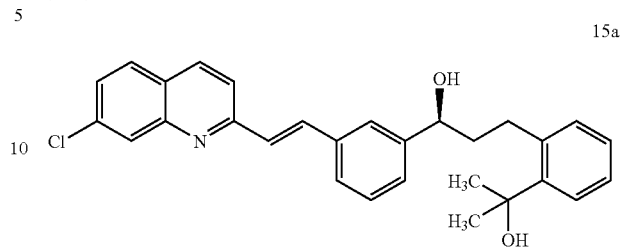

It should be noted that a better alternative of making (15) from (15a) comprises using an acetyl group for OH-protection instead of the tert.butyl dimethyl silyl group offered in the Ex 146. Such a process provides for higher yields and uses cheaper reagents. For details of such an improved process, see the Preparation 1 below.

The OH— group in Compound (15) is first converted into a leaving group L, typically an alkyl- or arylsulfonyloxy group such as C1-C4-alkylsulfonyloxy or (an optionally substituted)aryl-sulfonyloxy group. A suitable example is a mesyloxy group (compound (16a))

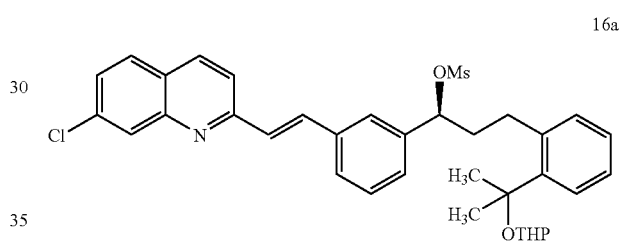

The mesylation reaction comprises contacting compound (15) with methanesulfonyl chloride in an inert solvent in the presence of a suitable base. By analogous means, other L-donating groups can be reacted with compound (15) to provide the desired leaving group.

The compound of formula (16) is converted to a compound of formula (17) by reaction with a thioacetic acid or a salt thereof, preferably sodium or potassium thioacetate, whereby the labile L- group is replaced by CH₃—CO—S— group; the reaction proceeds in a suitable inert solvent (toluene, dimethylformamide or mixtures thereof), preferably at temperatures close to and including ambient.

In the last step, the compound (17) is deprotected to form (6) by treatment with a strong acid, e.g. p-toluenesulfonic acid, in a suitable inert solvent, e.g. in an alcohol, ester, ether or ketone or mixtures thereof. The approximate yield of the whole sequence of making (6) starting from (15) can be about 60% or more.

A second reaction pathway starts from a methyl ester (18) as shown in the following reaction scheme:

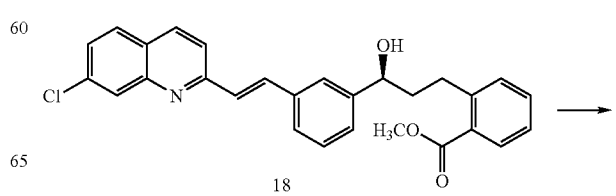

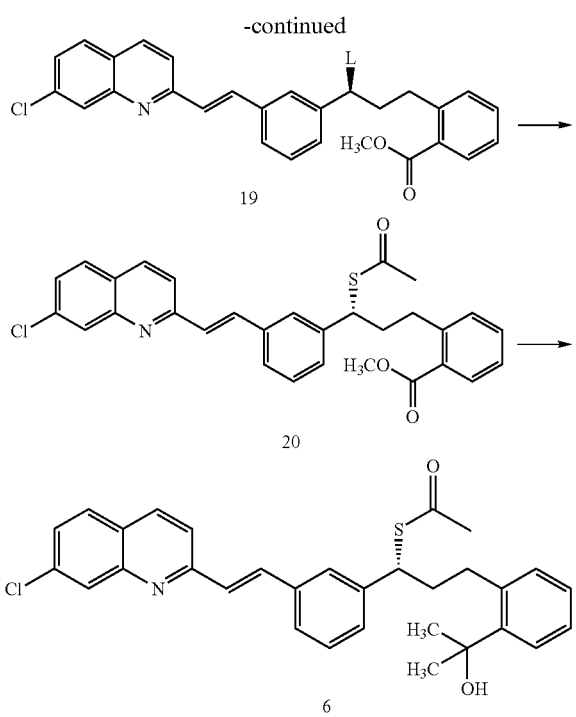

The compound (18) is also a known compound of the prior art (see Compound XXVII in EP 480717) and can be produced by method E in EP 480717 (see also steps 1 and 2 in Example 146). It can be isolated in solid form as a monohydrate.

Generally as in the first pathway, the OH— group is first made labile by converting it into a reactive group L such as an alkyl- or aryl sulfonyloxy group, preferably a mesyloxy group. The compound bearing the mesyloxy group (19a)

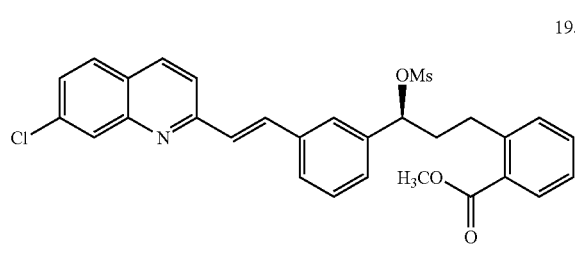

is preferred. The mesylation reaction comprises contacting compound (18) with methanesulfonyl chloride in an inert solvent in the presence of a suitable base, e.g. a tertiary amine such as triethylamine.

The labile compound (19) is then converted into acetylthio ester compound (20) by reaction with a thioacetic acid or salt thereof, preferably sodium or potassium thioacetate, in an inert solvent, essentially under the same conditions disclosed above for making compound (17). The resulting acetylthio ester compound (20) is subjected to a reaction with methyl lithium in an inert solvent such as tetrahydrofuran, to form compound (6).

The compound (6) may be isolated in a solid state and/or purified by conventional means before the cleavage reaction/conversion to compound (4). The solid state form of the compound (6) is a preferred form of that compound as far as the storage and handling is concerned. Accordingly, compound (6) can be used as a useful starting material for making montelukast and its salts.

The compound of formula (5) can be made by a variety of methods. For example, where R is hydrogen in formula (5), the method generically taught in Method M of U.S. Pat. No. 5,565,473 can be used. A process to make formula (5) wherein R represents a C1-C4 alkyl, specifically methyl, was suggested in the context of making a mercapto derivative in U.S. Pat. No. 5,565,473 (See Method R which produces methyl 1-mesyloxy cyclopropane 1-carboxylate (compound 5a in the present invention) on route to forming 1-(mercaptomethyl)cyclopropaneacetic acid ester compound). This process as shown in Example 161 of U.S. Pat. No. 5,565,473 starts with diethyl 1,1-cyclopropanedicarboxylate (A) and the first seven steps thereof are shown below:

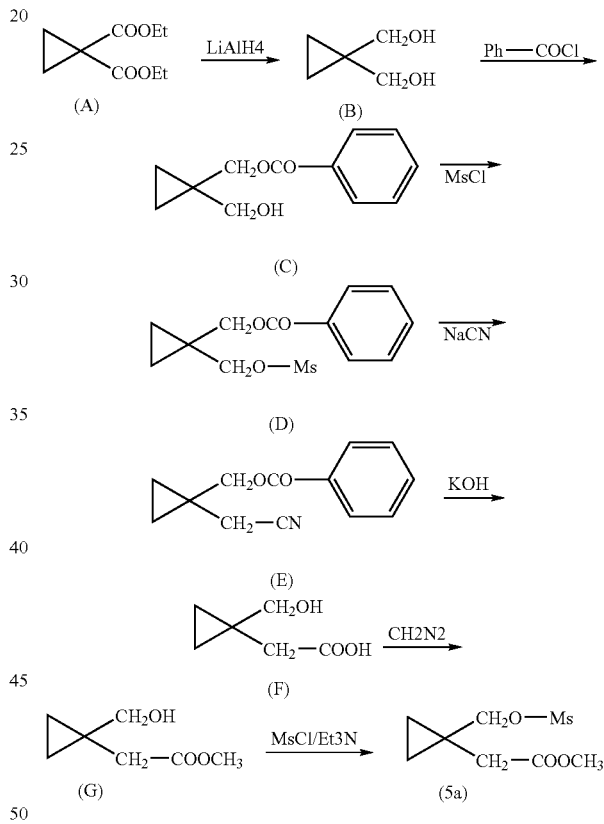

While such a reaction scheme can be used to obtain a compound of formula (5a), it is not advantageous. The main problem in obtaining the compound (5a) and, in analogy, any compound of the general formula (5), by this method is the low overall yield caused by the impossibility of obtaining selective monobenzoyl protection of the diol (B). The disclosed process (step 2 of Example 161), provides only a mixture of mono- and di-benzoylated diol in approximately equal yield. Apart from the fact that approx. 50% of the starting material is thereby lost, the resulting mixture of diols has to be resolved by two-fold column chromatography, which is inconvenient for scaling up.

Accordingly, the present invention provides for improved processes for making the compounds of formula (5) wherein R is C1-C4 alkyl. One reaction scheme is set forth below:

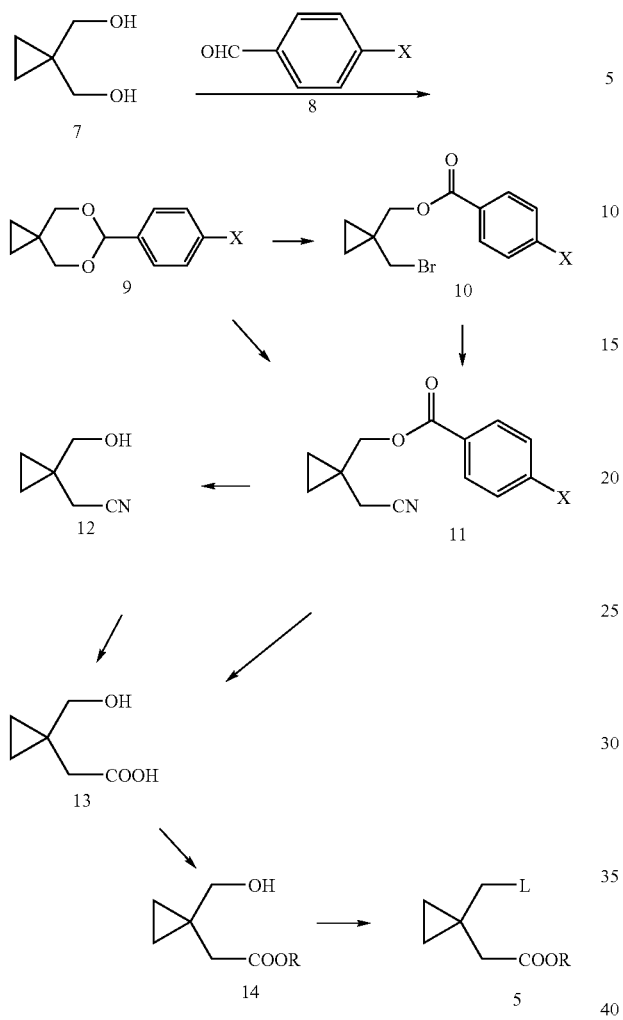

compound (8), wherein X is hydrogen, hydroxy, methoxy, halo, methyl, trifluoromethyl or nitro group, preferably the methoxy group, under conditions susceptible to form an acetal, whereby the OH— protection in the form of an acetal, has the substantial advantage that selective deprotection can be done stepwise. That is, in a first deprotection step only one OH— group is liberated and subjected to further reactions, while the remaining one remains protected for the desired time and is liberated only at the moment of need. Thus the formation and use of the compound of formula (9) is a particular aspect of the invention, especially in forming the compound (5).

A useful benzaldehyde compound (8) for the above protection is p-anisaldehyde (8a) (compound 8, X=methoxy)

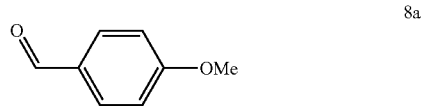

which has the advantage that the resulting acetal (9a)

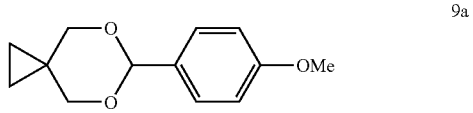

may be isolated as a solid material and may be purified from the excess of reagents and side contaminants.

The reaction between (7) and (8), preferably (8a), normally proceeds in a suitable non polar solvent such as benzene, toluene, hexane or cyclohexane at temperatures up to reflux and is either catalysed by an acid, particularly by p-toluenesulfonic acid, or proceeds under neutral conditions catalysed by, e.g., pyridinium p-toluene sulfonate (PPTS). The water formed by the reaction is advantageously removed, e.g. by azeotropic distillation, by a molecular sieve or by any other conventional process.

The next step comprises the oxidative opening of the acetal (9) under formation of the protected nitrile (11). Suitable oxidant is DDQ or p-chloranil; water present in the reaction mixture should be avoided. In the presence of water, partial or complete deprotection may be obtained yielding the undesired alcohol or diol. From practical reasons, the reaction may be performed stepwise. In the first step, the oxidative opening of the acetal ring in an anhydrous environment is performed in the presence of a bromide donor having a character of Lewis acid to produce the protected bromo compound (10). Suitable bromide donors, optionally in combination with a Lewis acid, include $CuBr_2$, LiBr, and a combination of $Bu_4NBr/CuBr_2$. About one molar equivalent of DDQ is sufficient, as higher amounts generally do not increase the speed and yield of the reaction. Suitable solvent for the reaction is an aprotic solvent, e.g. 1,2-dichloroethane, toluene or dichloromethane; the reaction readily proceeds even at ambient temperature but may be speeded up by heating the mixture up to the boiling point; however higher temperatures often cause the formation of impurities.

The monobenzoyl bromo derivative (10) may be advantageously purified from side products (particularly from monobenzoyl alcohol) by conventional means, e.g. by chromatography on silica gel, but can be used in the next step in a crude state as well.

The scheme comprises
a) protection of both OH— groups in 1,1-cyclopropane dimethanol (7) by a benzaldehyde compound (8) to yield a cyclic acetal compound (9);
b) oxidative opening of (9) under formation of mono-benzoyl nitrile compound (11), preferably via a monobenzoyl bromo compound (10);
c) deprotection of the OH— group and hydrolysis of the cyano group in (11) to yield the hydroxymethyl carboxylic acid compound (13), preferably via the hydroxymethyl nitrile compound (12);
d) esterification of the acid (13) with an C1-C4 alcohol in a presence of an acid to yield an ester compound (14); and
e) conversion of the ester (14) into the labile ester compound (5).

X is hydrogen, hydroxy, methoxy, chloro, bromo, fluoro, methyl, trifluoromethyl or nitro group; L is a leaving group typically a halogen or an alkyl- or aryl-sulfonyloxy group such as chloro, bromo, mesyloxy, besyloxy or tosyloxy group; and R is a C1-C4 alkyl group. Preferably, X=methoxy, L=bromo or mesyloxy and R is ethyl group.

This first scheme for making the starting ester compound of formula (5) relates to the surprising discovery that 1,1-cyclopropane dimethanol (7) may react with a benzaldehyde Reaction of the monobenzoyl bromo derivative (10) with metal cyanide, e.g. sodium or potassium cyanide yields the protected nitrile compound (11). The reaction proceeds in a suitable solvent, e.g. ethanol/water mixture.

If a cyanide is used instead of the bromide donor in the oxidative opening of compound (9), the reaction may directly lead to the protected nitrile (11), without forming and isolating the protected bromide.

Upon treatment of the protected nitrile (11) with a base, e.g. with sodium or potassium hydroxide, the benzoyl group may be removed and a deprotected nitrile (12) is formed. Simultaneously, the cyano group in (12) is susceptible to a hydrolysis by the base. The final product of deprotection and hydrolysis is, after neutralization of the alkaline environment and removal of inorganic side products, the hydroxymethyl carboxylic acid (13). For practical reasons, the reactions may be advantageously performed stepwise in as much as the split-off benzoic acid can be better removed from the product in the stage of the nitrile compound (12). For instance, the nitrile can be extracted well from the alkaline reaction medium by a non-polar solvent. Thus, it is generally preferred to use mild conditions for the treatment with a base, under which only the deprotection occurs (a temperature close to ambient), to purify the obtained deprotected nitrile (12) from the liberated side product comprising the original protective group, and then to carry out the hydrolysis of the nitrile group. The nitrile hydrolysis may be performed, e.g., by heating the nitrile with an alkali metal hydroxide in water, lower alcohol or in a mixture of both. After neutralization of the alkaline environment used for the hydrolysis, the acid (13) is obtained. It may be isolated as a solid product and/or purified by conventional means, for instance by crystallization from a suitable solvent, for instance from ethyl acetate. Solid crystalline form of the acid (13) is another aspect of the present invention.

In the next step, the acid (13) is esterified. For methyl esters, this can be carried out as shown in Example 161 of U.S. Pat. No. 5,565,473 (see also compound (f) in the Example 161 reaction scheme shown above) by treatment of the acid compound with diazomethane to yield the methyl ester (14a) (compound 14, R=$CH_3$). But, diazomethane is a toxic and explosive compound and can only form the methyl ester. Surprisingly, it has been discovered that the hydroxymethyl acid (13), which is expected to be sensitive to acidic environment/conditions, can be esterified by conventional techniques including by treatment with a corresponding alcohol under catalysis of a strong acid. This allows for a more safe and convenient way for an industrial process and, moreover, it allows to produce a variety of esters of formula (14), not only the methyl ester (14a). The preferred ester is the methyl ester (14a) or ethyl ester (14b) formed by using methanol and ethanol, respectively.

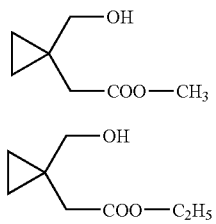

14a

14b

Furthermore, no column chromatography is required within the above process.

In the last step, the ester (14), for instance the methyl ester (14a) or ethyl ester (14b), is converted into the labile ester (5) (R=C1-C4 alkyl) by methods known per se. The labile group L preferably comprises bromo- or mesyloxy group. Preferred compounds of formula (5) are compounds (5a) to (5d).

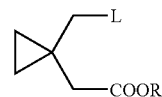

5

5a: L = O—Ms and R = $CH_3$
5b: L = O—Ms and R = $C_2H_5$
5c: L = Br and R = $CH_3$
5d: L = Br and R = $C_2H_5$ For instance, the compounds (5a) and (5b) may be made by reacting the corresponding ester of formula (14) with a mesylchloride.

It should be noted that an intermediate in the acid catalyzed esterification may be a lactone (22)

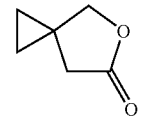

(22)

which may be formed by a treatment of the acid (13) with the strong acid. It may be possible to form and/or isolate the lactone compound by treating the compound (13) with a strong acid alone. The lactone ring will subsequently open under the formation of the desired ester by adding an alcohol under acid catalysis conditions, i.e. in the presence of the strong acid, etc. Further, the L group donor may also be added with the alcohol such that from the lactone both the R group and L group are added in a single reaction step. This allows for a more direct route for making the compounds (5), especially where L is a bromo group, by reacting the lactone with, e.g., hydrogen bromide in a corresponding alcohol such as methanol or ethanol.

A second general process for making the ester compounds of formula (5) involves converting the starting compound of formula (7) into a compound of formula (12) by a different route than above. This second process can be represented by the following scheme:

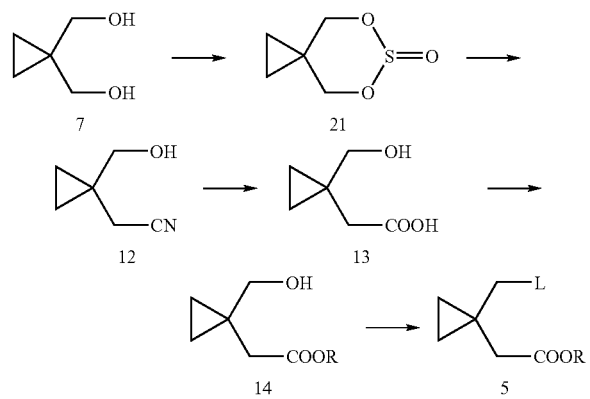

The scheme comprises:
a) reacting 1,1-cyclopropane dimethanol (7) with thionyl chloride or with a dialkyl sulfite, wherein each alkyl group is a C1-C4 alkyl, to yield a compound of formula (21);
b) reacting the compound (21) with an alkali metal cyanide to form a compound (12);
c) hydrolyzing the cyano group in the compound (12) to form a hydroxymethyl carboxylic acid compound (13);
d) esterification of the acid (13) with an C1-C4 alcohol in a presence of an acid to yield an ester compound (14); and
e) conversion of the ester (14) into the labile ester compound (5).

In the first step, the compound (7) reacts with thionyl chloride or with a dialkyl sulfite, preferably dimethyl sulfite or di-isopropylsulfite to yield a cyclic sulfite compound (21). The alkyl groups are generally the same, although different alkyls are not excluded. The compound (21) is generally isolated as a solid product and, if desired, purified from side products. Whether isolated or not, the compound of formula (21) is then reacted with an alkaline metal cyanide, preferably with sodium cyanide, to form the compound of formula (12). Both of these steps (a) and (b) can be performed using the conditions described in U.S. Pat. Nos. 5,270,324 or 5,523,477 for the thionyl chloride-based or the dialkyl sulfite-based variant, respectively. The obtained nitrile of formula (12), typically in an isolated form, is then transformed into the compound (5) as described above for the first general process.

The esters (5) can then be coupled with the compound (4) to form the esters of montelukast (formula (1a)) as described above. Deprotection of the ester of montelukast of formula (1a), such as by hydrolysis with base followed by acidification, etc., results in montelukast or a salt thereof.

The invention is further described by way of the following non-limiting examples.

EXPERIMENTAL

Preparation 1—Synthesis of 2-(2-(2-(3(S)-(3-(2-(7-chloro-2-quinolinyl)-ethenyl)phenyl)-3-hydroxypropyl)phenyl)-2-propoxy) tetrahydropyran [compound (15)] from 2-(2-(3(S)-(3-(2-(7-chloro-2-quinolinyl)-ethenyl)phenyl)-3-hydroxypropyl)phenyl)-2-propanol [compound 15a] via an acetate a)
The Diol compound (15a) was dissolved in dichloromethane (10 g in 200 ml), 2.59 g of pyridine and a catalytic amount of 4-dimethylaminopyridine were added under stirring and finally 3.34 g of acetic anhydride was added dropwise to the stirred mixture. The reaction was completed, according to TLC, after 20 minutes at room temperature. 150 ml of ice-cold water was added and the mixture was stirred for 15 minutes. After separation of layers, the water layer was extracted with 50 ml of dichloromethane. The combined layers were washed successively with water (150 ml), saturated NaHCO3 solution (150 ml) and water (150 ml), dried over anhydrous sodium sulfate, filtered and evaporated to dryness yielding 13.0 g of product.

b)
13 g of the acetate from the step a) was dissolved in 225 ml of dichloromethane. Under stirring, 9.19 g of 3,4-dihydro-2H-pyran and 0.94 g of triphenylphosphonium bromide were added. The reaction mixture was heated under reflux for 32 hours. Then, 4.60 g of 3,4-dihydro-2H-pyran and 0.90 g of triphenylphosphonium bromide were added and the mixture was refluxed for next 24 hours. The mixture was cooled, 200 ml of water were added and the organic layer was separated, washed with 2×200 ml of brine, dried over anhydrous sodium sulfate, filtered and evaporated to dryness yielding 16.3 g of the product.

c)
16.2 g of the product from the step b) was dissolved in 75 ml of tetrahydrofuran. A solution of 2 g of sodium hydroxide in 250 ml of methanol was added under stirring. The reaction mixture was stirred at room temperature for 1 hour. According to TLC, the reaction was completed. The reaction mixture was neutralized and concentrated to approx. 50 ml. 200 ml of dichloromethane and 200 ml of water were added to the concentrate. Organic phase was separated, washed with 2×200 ml of water, dried over anhydrous sodium sulfate, filtered and evaporated to dryness. Purification of the resulting oil by column chromatography (Merck silica gel 60, eluens heptane/ethyl acetate 2/1) afforded the desired compound as a pale yellow product.

Isolated yield: 10.1 g (85% over three steps).
$^1$H NMR and $^{13}$C NMR confirmed the expected structure.

EXAMPLE 1

Synthesis of 2-(2-(3(S)-(3-(2-(7-chloro-2-quinolinyl)-ethenyl)phenyl)-3(acetylthio)propyl)phenyl)-2-propanol [compound (6)]

a)
The compound (15) from Preparation 1 (5 g) was dissolved in 75 ml of dry dichloromethane. The solution was cooled to −40° C. Then, 1.37 g of methanesulfonylchloride and 1.40 g of triethylamine were added under stirring. The yellow suspension was stirred at −40° C. for 30 minutes and then at 0° C. for 1 hour. The reaction mixture was washed with 2×75 ml of water, the organic layer was dried over anhydrous sodium sulfate, filtered and evaporated to dryness.

b)
The residue from the step a) was dissolved in a mixture of 60 ml of toluene and 20 ml N,N-dimethylformamide. 1.24 g of potassium thioacetate was added and the reaction mixture was stirred overnight at room temperature. 75 ml of ethyl acetate and 75 ml of water were added. The layers were separated and the water layer was washed with 40 ml of ethyl acetate. The combined organic layers were washed with 2×75 ml of brine, dried over anhydrous sodium sulfate, filtered and evaporated into dryness.

c)
The evaporated residue from step b) was dissolved in a mixture of 60 ml of methanol and 20 ml of tetrahydrofuran. 1.0 g of p-toluene sulfonic acid monohydrate was added under stirring. The reaction mixture was stirred for 3 days at room temperature. 75 ml of water and 95 ml of ethyl acetate were added to the mixture and layers were allowed to separate. The water layer was washed with 40 ml of ethyl acetate and the combined organic layers were washed with 2×75 ml of brine. The organic layer was dried over anhydrous sodium sulfate, filtered and evaporated to dryness. Purification of the resulted oil by column chromatography (Merck silica gel 60, eluens heptane/ethyl acetate 2/1) afforded the desired compound as a pale yellow product.

Isolated yield: 3.0 g (63% over three steps).
1H NMR and 13C NMR confirmed the expected structure.

EXAMPLE 2

Ethyl 1-mesyloxymethyl cyclopropane acetate (5b)

Step 1—1,1-cyclopropanedimethanol O-p-methoxybenzylidene acetal (compound 9a)

3.63 g 1,1-cyclopropanedimethanol was dissolved in 50 ml of cyclohexane. 4.85 g p-anisaldehyde and 250 mg p-toluenesulfonic acid were added. The mixture was heated to reflux and water was distilled off azeotropically. After two hours, the mixture was allowed to cool to room temperature and left overnight. Cyclohexane was removed at reduced pressure, affording a yellow oil. The crude product was dissolved in ethyl acetate and washed with saturated bicarbonate solution and brine, dried with sodium sulfate and concentrated. The resulting crude product mixture was crystallised from ethanol, affording 700 mg 1,1-cyclopropanedimethanol O-p-methoxybenzylidene acetal as slightly yellow crystals.

Step 2—1-(p-methoxybenzoyloxy)methyl 1-bromomethyl cyclopropane (compound 10a)

1 mmol of the acetal from the Step 1 was dissolved in 5 ml of 1,2-dichloroethane (distilled with calcium chloride, stored on molecular sieves) under nitrogen atmosphere. 1 mmol copper(II)bromide and 1 mmol tetrabutyl ammonium bromide were added and the mixture was stirred for 30 min. at room temperature. The oxidizing agent (DDQ or chloranil; 1-2 mmole) is added and the mixture is stirred until the starting material has disappeared on TLC. Ethyl acetate is added to the reaction mixture at room temperature and washed twice with a saturated aqueous bicarbonate solution. After concentration of the organic phase, the crude product is obtained.

For analytical purposes, the crude product is dissolved in heptane/ethyl acetate: 4/1 and eluted over silica. The filtrate is dried ($Na_2SO_4$) and evaporated to give the title product.

Step 3—the 1-(p-methoxybenzoyloxymethyl)cyclopropane-1-acetonitrile (11a)

261 mg of compound 10a was dissolved in 5 ml ethanol. A solution of 98 mg potassium cyanide in 5 ml water was added and the mixture was stirred at 35° C. for two days. 10 ml of a saturated aqueous sodium bicarbonate was added. The mixture was extracted twice with ethyl acetate. The combined extracts were dried with sodium sulfate and evaporated to give a yellow liquid. Purification with column chromatography (heptane/ethyl acetate 3/1) gave the title compound (38 mg) confirmed by NMR and LC/MS Step 4—1-(hydroxymethyl)-cyclopropane-1-acetonitrile (12)

0.16 mol of the compound (11a) was dissolved in 250 ml of ethanol and 250 ml of 4M aqueous potassium hydroxide was added. The mixture was stirred for 90 minutes at room temperature. Ethanol was evaporated and the remaining aqueous solution was extracted twice with 250 ml of dichloromethane. The combined organic layers were washed twice with 250 ml of aqueous sodium bicarbonate and once with 250 ml of brine. Drying the organic layer over anhydrous sodium sulfate and evaporating gave the title compound as an orange liquid (16.2 g).

Step 5: 1-(hydroxymethyl) cyclopropane acetic acid (13)

15.6 g of the compound (12) was dissolved in 100 ml of ethanol. 150 ml of 8M aqueous potassium hydroxide was added and the mixture was stirred at reflux for 17 hours. Ethanol was evaporated and the remaining aqueous solution was cooled to 2° C. Concentrated hydrochloric acid was added dropwise at a temperature of 4-6° C. When the pH decreased to below 1, the aqueous mixture was decanted from the white precipitate and extracted four times with 125 ml of ethyl acetate. The solid was thoroughly washed with ethyl acetate. The combined ethyl acetate layers were dried over anhydrous sodium sulfate and evaporated to give title compound as a crude product (8.9 g).

For analytical purposes, the crude product was crystallised from ethyl acetate (1.2 g of crystals were obtained). The mother liquor was evaporated and the recovered crude product was used in the esterification reaction. (7.4 g).

Step 6: Ethyl 1-hydroxymethyl cyclopropane acetate (14b)

7.1 g of crude (13) product was dissolved in 150 ml of ethanol. 1 ml of concentrated sulfuric acid was added and the solution was stirred at reflux for 2 hours. 50 ml of saturated aqueous sodium bicarbonate was added to the cooled mixture and the mixture was extracted twice with 100 ml of dichloromethane. The combined organic extracts were dried over anhydrous sodium sulfate and evaporated. The crude product was distilled at 100° C. at a reduced pressure affording a slightly yellow liquid (3.2 g).

Step 7 Ethyl 1-mesyloxymethyl cyclopropane acetate (5b)

253 mg of compound 14b and 225 µl triethylamine were dissolved in 10 ml dichloromethane and cooled to −50° C. 140 µl methanesulfonylchloride was added and the mixture was stirred for one hour allowing the temperature to increase to 0° C. Saturated aqueous sodium bicarbonate was added and the mixture was extracted twice with dichloromethane. The organic extracts were combined and dried with sodium sulfate. Evaporation of the solvent gave 308 mg of the title compound as an almost colourless liquid.

Structure confirmed by NMR.

EXAMPLE 3

Synthesis of Montelukast Ethyl Ester (Compound (1a/2))

250 mg of the compound (6) was dissolved in 5 ml of acetonitrile and nitrogen was bubbled through the solution for 10 minutes. At 0° C., 28.5 mg of hydrazine monohydrate was added. The solution was stirred at 0° C. for 1 hour.

The solution was added to a cold (0° C.) suspension of the 114 mg of ethyl 1-mesyloxymethyl cyclopropane acetate (5b) and 316 mg of cesium carbonate in 5 ml of acetonitrile, through which nitrogen was bubbled for 10 minutes. The suspension was stirred at 0° C. for 30 minutes and was then allowed to warm to room temperature. Reaction progress was monitored by TLC. The reaction mixture was kept overnight at room temperature. 30 ml of ethyl acetate and 30 ml of water were added. The organic phase was washed with 2×30 ml of brine, dried over anhydrous sodium sulfate, filtered and evaporated to dryness. Purification of the yellow oil by column chromatography (Merck silica gel 60, eluens heptane/ethyl acetate 2/1) afforded the desired compound as an oil.

1H and 13C NMR spectrum confirmed the expected structure.

EXAMPLE 4A

Synthesis of Compound (20)

Step 1A: Synthesis of Compound (19)

3 g of the compound (18) (monohydrate) was slurried in 100 ml of toluene and was azeotropically dried under reduced pressure. The resulting brown oil was dissolved in 75 ml of dry dichloromethane. The solution was cooled to −40° C. Then 938 mg methanesulfonyl chloride and 957 mg triethylamine were added. The orange/brown solution was stirred at −40° C. for 30 minutes and at 0° C. for 1 hour. The reaction mixture was washed with 2×75 ml water. The organic layer was dried ($Na_2SO_4$), filtered, and evaporated to dryness resulting in an orange/brown oil.

Step 2A: Synthesis of Compound (20)

The oil was dissolved in 36 ml toluene and 12 ml DMF and then 849 mg of potassium thioacetate was added and the reaction mixture was stirred over night at room temperature. TLC showed a slight amount of starting material. 75 ml of ethyl acetate and 75 ml water were added. The water layer was washed with 20 ml ethyl acetate. The combined organic layers were washed with 2×75 ml water, dried ($Na_2SO_4$), filtered and evaporated to dryness, resulting in 3.85 g of a brown oil. The crude product was purified by column chromatography using Silica (20-45 micron) and heptane/ethyl acetate (85/15→80/20) as eluens. Pure fractions were collected and evaporated to dryness, resulting in a yellow oil.

Isolated yield: 1.87 g (57%)
$^1$H- and $^{13}$C-NMR confirmed the expected structure

EXAMPLE 4B

Synthesis of Compound (20)

Step 1B: Synthesis of Compound (19)

5 g of the compound (18) (monohydrate) was slurried in 120 ml of toluene and was azeotropically dried under reduced pressure. The resulting brown oil was dissolved in 80 ml of dry toluene. The solution was cooled to −40° C. 1.56 g methanesulfonyl chloride and 1.59 g triethylamine were added. The reaction mixture was stirred at −40° C. for 45 minutes and then at 0° C. for 45 minutes. The reaction mixture was washed with 2×100 ml brine. The organic layer was dried ($Na_2SO_4$), filtered, and evaporated to dryness, resulting in an orange/brown oil.

Step 2B: Synthesis of Compound (20)

The oil was dissolved in 60 ml of toluene and 20 ml of dimethylformamide. Then 1.42 g potassium thioacetate was added and the reaction mixture was stirred over night at room temperature. TLC showed still a slight amount of starting material. The reaction mixture was stirred for 24 hrs at RT. TLC showed still a slight amount of starting material. 80 ml of ethyl acetate and 80 ml of water were added. The water layer was washed with 20 ml ethyl acetate. The combined organic layers were washed with 2×80 ml water, dried ($Na_2SO_4$), filtered, and evaporated to dryness, resulting in 6.1 g of a brown oil. The crude product was purified by column chromatography using Silica (20-45 micron) and heptane/ethyl acetate (85/15→80/20) as eluens. Pure fractions were collected and evaporated to dryness, resulting in a yellow oil.

Isolated yield: 3.69 g (68%)
$^1$H-NMR: confirmed the expected structure

EXAMPLE 5

Synthesis of 2-(2-(3(S)-(3-(2-(7-chloro-2-quinolinyl)-ethenyl)phenyl)-3(acetylthio)propyl)phenyl)-2-propanol [compound (6)] from compound (20)

200 mg of the compound (20) was dissolved in dry THF (5 ml) and the yellow solution was cooled to −78° C. 0.97 ml of Methyllithium (1.6 M in $Et_2O$) was added dropwise. The color of the solution went from yellow to orange/brown. According to TLC the reaction was completed (almost) immediately. Ammonium chloride (spatula) was added and while allowing the reaction mixture to warm to room temperature, 25 ml ethyl acetate and 25 ml water were added. The yellow organic layer was washed with 2×25 ml brine, dried (Na2SO$_4$), filtered, and evaporated to dryness, resulting in 183 mg of a yellow oil.

The crude product was purified by column chromatography using Silica (20-45 micron) and heptane/ethyl acetate (90/10→85/15) as eluens. Pure fractions were collected and evaporated to dryness, resulting in a yellow solid.

Isolated yield: 23 mg
$^1$H- and $^{13}$C-NMR confirmed the expected structure

Each of the patents, articles, and publications mentioned above is incorporated herein by reference in its entirety. The invention having been thus described, it will be obvious to the worker skilled in the art that the same may be varied in many ways without departing from the spirit of the invention and all such modifications are included within the scope of the present invention as set forth in the following claims.

What is claimed is:

1. A process for making montelukast or its salt, which comprises cleaving a compound of formula (6)

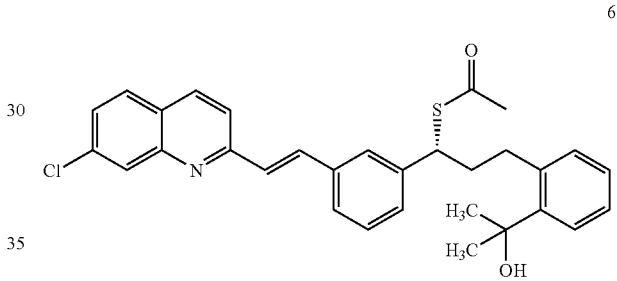

by hydrazine or sodium methoxide, to form a compound of formula (4)

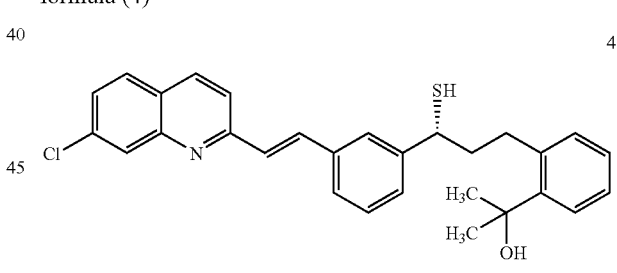

and converting said compound of formula (4) into montelukast of formula (1)

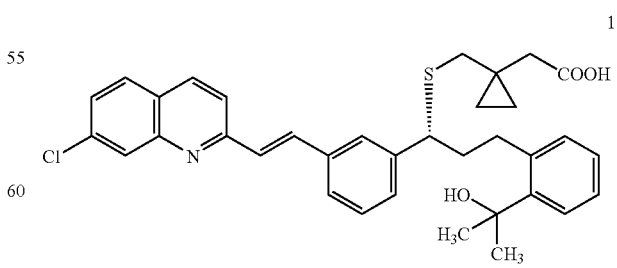

or a salt thereof.

2. The process according to claim 1, wherein said conversion comprises reacting said compound of formula (4) with a compound of formula (5)

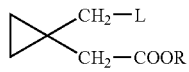
(5)

wherein R is hydrogen or C1-C4 alkyl group, and L is a leaving group.

3. The process according to claim 2, wherein L is a group selected from the group consisting of a chloro, bromo, mesyloxy, besyloxy, and tosyloxy group.

4. The process according to claim 2, wherein R in the compound of formula (5) is a C1-C4 alkyl group and said reaction of the compound of formula (4) with the compound of formula (5) produces a compound of formula (1a)

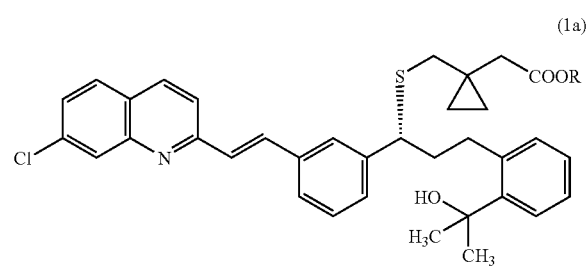
(1a)

and said conversion further comprises convening the ester group in the compound of formula (1a) into a carboxylic acid or salt group to form said compound of formula (1).

5. The process according to claim 4, wherein the L group in formula (5) is a bromo or mesyloxy group and the K group is a methyl or ethyl group.

6. The process according to claim 2, wherein said reaction is carried out in acetonitrile and under an inert atmosphere of nitrogen or argon gas.

7. The process according to claim 1, wherein the produced compound of formula (4) is not isolated prior to reacting with said compound (5).

8. The process according to claim 1, which further comprises making said compound of formula (6) by the process which comprises:

a) converting a compound of formula (15)

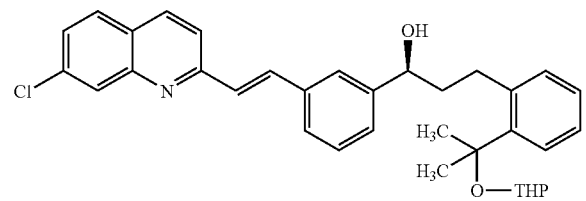
15 wherein THP means a tefrahydropyranyl group, into a compound of formula (16)

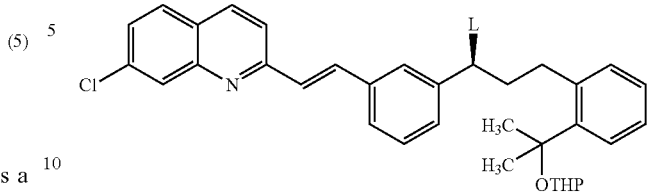
16 wherein L is a leaving group, b) reacting said compound of formula (16) with thioacetic acid or a salt thereof to yield a compound of formula (17),

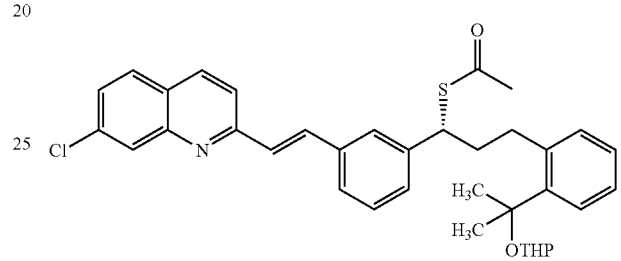
17 c) removing the THP group from said compound of formula (17) to form said compound of formula (6); and, d) optionally, isolating said compound of formula (6) from the reaction mixture before said cleaving step is performed.

9. The process according to claim 1, which further comprises making said compound of formula (6) by the process which comprises:

a) converting a compound of formula (18)

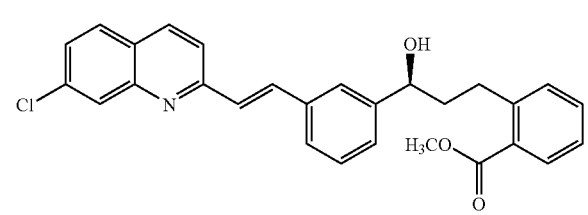
18 into a compound of formula (19)

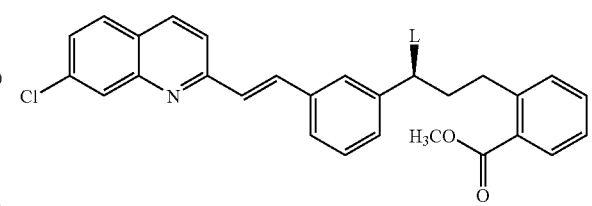
19 wherein L is a leaving group;

b) reacting said compound of formula (19) with thioacetic acid or a salt thereof to yield a compound of formula (20);

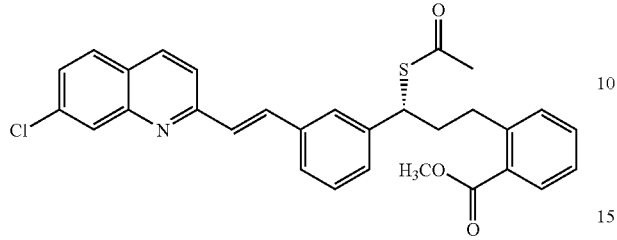

c) reacting the compound of formula (20) with methyl lithium to form said compound of formula (6); and, d) optionally, isolating the compound of formula (6) from the reaction mixture before said cleaving step is performed.

10. A process of forming a compound of formula (5), which comprises:

a) reacting 1,1-cyclopropane dimethanol of formula (7)

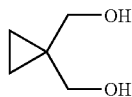

with a benzaldehyde compound of formula (8)

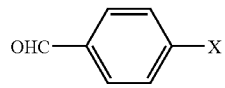

wherein X is hydrogen, hydroxy, methoxy, chloro, bromo, fluoro, methyl, trifluoromethyl or nitro group, to yield a cyclic acetal compound of formula (9);

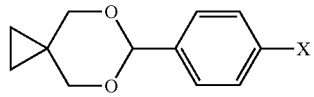

b) converting, in the presence of an oxidant, the compound of formula (9) to a mono-benzoyl nitrile compound of formula (11);

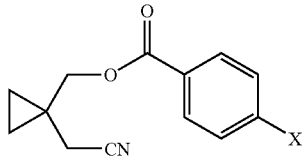

c) deprotecting the OH— group and hydrolyzing the cyano group in the compound of formula (11) to form a hydroxymethyl carboxylic acid compound of formula (13);

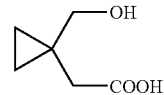

d) esterifying the acid compound of formula (13) with a C1-C4 alcohol in the presence of an acid to yield an ester compound of formula (14)

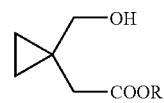

wherein R is a C1-C4 alkyl group; and e) converting the ester compound of formula (14) into a compound of formula (5)

wherein R is a C1-C4 alkyl group and L is a leaving group.

11. The process according to claim 10, wherein the benzaldehyde compound of formula (8) is p-anisaldehyde.

12. The process according to claim 10 wherein said converting step (b) comprises first converting said compound of formula (9) into a compound of formula (10)

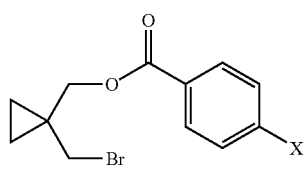

and subsequently reacting said compound of formula (10) with a metal cyanide to form said compound of formula (11).

13. The process according to claim 10, wherein R is an ethyl group and L is bromo or mesyloxy group.

14. A compound of formula (6):

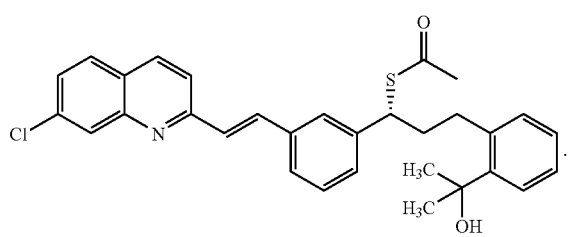

* * * * *